United States Patent
Kufe et al.

(10) Patent No.: US 7,118,862 B2
(45) Date of Patent: Oct. 10, 2006

(54) INDUCTION OF APOPTOSIS BY CELLULAR STRESS

(75) Inventors: Donald W. Kufe, Wellesley, MA (US); Rima Kaddurah-Daouk, Belmont, MA (US); Ralph R. Weichselbaum, Chicago, IL (US)

(73) Assignees: Dana-Farber Cancer Institute, Inc., Boston, MA (US); The University of Chicago, Chicago, IL (US)

( * ) Notice: Subject to any disclaimer, the term of this patent is extended or adjusted under 35 U.S.C. 154(b) by 643 days.

(21) Appl. No.: 10/125,003

(22) Filed: Apr. 18, 2002

(65) Prior Publication Data
US 2002/0182588 A1 Dec. 5, 2002

Related U.S. Application Data

(60) Provisional application No. 60/284,785, filed on Apr. 18, 2001.

(51) Int. Cl.
*C12Q 1/68* (2006.01)
(52) U.S. Cl. .............................. 435/6; 435/4; 435/7.2; 436/501; 436/518
(58) Field of Classification Search .................. 435/4, 435/7.1; 436/501
See application file for complete search history.

(56) References Cited

FOREIGN PATENT DOCUMENTS

| WO | WO 97/08184 | 3/1997 |
| WO | WO 98/03195 | 1/1998 |
| WO | WO 00/70091 | 11/2000 |

OTHER PUBLICATIONS

Finucane et al., J Biol Chem, vol. 274, Issue 4, 2225-2233, Jan. 22, 1999.*
Green et al., (1998, Science, vol. 281, pp. 1309-1312).*
Konishi et al., "Activation of protein kinase C by tyrosine phosphorylation in response to $H_2O_2$," Proc. Natl. Acad. Sci. USA 94:11233-11237 (1997).
Majumder et al., "Mitochondrial Translocation of Protein Kinase C δ in Phorbol Ester-induced Cytochrome *c* Release and Apoptosis," J. of Biological Chemistry 275(29):21793-21796 (2000).
Sun et al., "Activation of the Cytoplasmic c-Abl Tyrosine Kinase by Reactive Oxygen Species," J. of Biological Chemistry 275(23):17237-17240 (2000).
Sun et al., "Interaction between Protein Kinase C δ and the c-Abl Tyrosine Kinase in the Cellular Response to Oxidative Stress," J. of Biological Chemistry 275(11):7470-7473 (2000).
Yuan et al., "Regulation of DNA damage-induced apoptosis by the c-Abl tyrosine kinase," Proc. Natl. Acad. Sci. USA 94:1437-1440 (1997).
Herr et al., "Cellular Stress Response and Apoptosis in Cancer Therapy," Blood., Nov. 2001, vol. 98, No. 9, pp. 2603-2614.
Ito et al., "Targeting of the c-Abl Tyrosine Kinase to Mitchondria in Endoplasmic Reticulum Stress-Induced Apoptosis," Molecular and Cellular Biology, Sep. 2001, vol. 21, No. 18, pp. 6233-6242.
Kharbanda et al., "Translocation of SAPK/JNK to Mitochondria and Interaction with Bcl-$X_L$ in Response to DNA Damage," Journal of Biological Chemistry, Jan. 2000, vol. 275, No. 1, pp. 322-327.

* cited by examiner

*Primary Examiner*—Misook Yu
(74) *Attorney, Agent, or Firm*—Fish & Richardson P.C.

(57) ABSTRACT

The invention provides methods of screening to identify compounds that modulate the ability of a protein to translocate to the mitochondria when a cell is subjected to cellular stress. Such compounds can be useful to modulate the level of apoptosis in a cell. For example, compounds identified according to the methods described herein can be used to treat disorders characterized by excessive apoptosis, e.g., a neurological disorder, or insufficient apoptosis, e.g., cancer.

19 Claims, No Drawings

INDUCTION OF APOPTOSIS BY CELLULAR STRESS

CROSS REFERENCE TO RELATED APPLICATIONS

This application claims priority from U.S. Provisional Application Serial No. 60/284,785, filed Apr. 18, 2001. The entire content of the prior application us incorporated herein by reference.

STATEMENT AS TO FEDERALLY SPONSORED RESEARCH

This invention was made with Government support under grant number CA42802 awarded by the National Cancer Institute. The Government may have certain rights in the invention.

FIELD OF THE INVENTION

The invention relates apoptosis, and in particular to the identification of compounds that modulate the translocation of proteins to the mitochondria upon the induction of cellular stress.

BACKGROUND OF THE INVENTION

Normal cellular metabolism is associated with the production of reactive oxygen species (ROS) and, as a consequence, damage to DNA and proteins. ROS have been implicated as signaling molecules that contribute to neurodegenerative diseases and aging. The generation of ROS is associated with apoptosis and certain cells, particularly neurons, are highly sensitive to this response. Studies have indicated that ROS-induced apoptosis is p53-dependent and that p53-induced apoptosis is mediated by ROS. In addition, the p66shc adaptor protein and the p85 subunit of phosphatidylinositol 3-kinase (PI3-K) have been implicated in the apoptotic response to oxidative stress.

Antioxidants have been proposed as one approach to diminish ROS damage to cells. Importantly, the signaling pathways responsible for ROS-induced apoptosis are for the most part unknown.

SUMMARY OF THE INVENTION

The invention is based, at least in part, on the discovery that, when a cell is subjected to a cellular stress, proteins such as protein kinase C delta (PKCd) and c-Abl are translocated into the mitochondria as part of the apoptotic program that eventually leads to cell death. The present invention provides methods of screening to identify compounds that modulate the ability of a protein to translocate to the mitochondria when a cell is subjected to cellular stress. Compounds identified according to the methods described herein can be used to treat disorders characterized by excessive apoptosis, e.g., a neurological disorder, or insufficient apoptosis, e.g., cancer.

The invention is also based, at least in part, on the discovery that the protein catalase is ubiquitinated and that the ubiquitination status and stability of catalase is regulated by its phosphorylation by c-Abl and Arg (a nonreceptor tyrosine kinase that has an overall structure similar to that of c-Abl). Catalase is a major effector in the regulation of intracellular ROS levels (see, e.g., Linton et al. (2001) Exp. Gerontol. 36:1503–18). In particular, catalase is an endogenous antioxidant enzyme that protects a cell from oxidative damage by degrading intracellular $H_2O_2$. Accordingly, the compositions and methods described herein can be used to modulate catalase levels and/or activity in a cell and therefore modulate ROS levels in the cell as well as the associated ROS-induced cell death.

In one aspect, the invention features a method of identifying a compound that inhibits mitochondrial translocation of a protein. The method includes the steps of: providing a cell; subjecting the cell to a cellular stress, wherein the cellular stress induces mitochondrial translocation of the protein; contacting the cell with a test compound; and determining whether mitochondrial translocation of the protein is decreased when the cell is contacted with the test compound, the decrease being an indication that the test compound inhibits mitochondrial translocation of the protein. The protein can be any protein, e.g., a protein kinase such c-Abl or PKCd, that translocates to the mitochondria upon the induction of cellular stress.

"Mitochondrial translocation of a protein" refers to the migration of a protein into the mitochondria from a location in the cell but outside of the mitochondria, e.g., from the cytoplasm, nucleus, or endoplasmic reticulum (ER). Mitochondrial translocation does not require that all species of a particular protein in a cell be translocated into the mitochondria. For example, mitochondrial translocation can include translocation of all or a portion of the species of a protein located in one compartment, e.g., the ER, whereas no translocation from another compartment, e.g., the nucleus, is detected.

A "test compound" can be any compound, synthetic or naturally occurring. Examples of test compounds, include but are not limited to peptides, polypeptide, antibodies, and small organic or inorganic molecules.

"Cellular stress" refers to a treatment that, when applied to a cell, induces cell death. Examples of cellular stresses include oxidative stress, endoplasmic reticulum stress, cytoskeletal stress, and genotoxic stress. Cellular stress can be induced by, for example, subjecting a cell to a compound, radiation, or a temperature that induces cell death.

"Oxidative stress" refers to a treatment that results in the generation of reactive oxygen species (ROS) within a cell. Examples of ROS include singlet oxygen, hydroxyl radicals, superoxide, hydroperoxides, and peroxides. One method of subjecting a cell to oxidative stress constitutes administering hydrogen peroxide ($H_2O_2$) to the cell.

"Endoplasmic reticulum stress" refers to a treatment that modulates a normal function of the ER. Generally, an ER stress results in the accumulation of unfolded proteins in the ER. Examples of ER stress include treatments that increase intracellular calcium pools or block transport of proteins from the ER to Golgi.

"Cytoskeletal stress" refers to a treatment that modulates a normal function of the cytoskeleton.

"Genotoxic stress" refers to a treatment that causes damage to the DNA of a cell. Examples of agents that induce genotoxic stress include ionizing radiation and mutagenic compounds.

In one embodiment, the cellular stress includes oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

One example of a method described herein is a method of identifying a peptide that inhibits mitochondrial translocation of c-Abl, including the steps of: providing a cell; contacting the cell with $H_2O_2$; further contacting the cell with a peptide; and determining whether mitochondrial translocation of c-Abl is decreased when the cell is contacted with the peptide, the decrease being an indication that the peptide inhibits mitochondrial translocation of c-Abl.

In another aspect, the invention features a method of identifying a compound that increases mitochondrial translocation of a protein. The method includes the steps of: providing a cell; contacting the cell with a test compound; and determining whether mitochondrial translocation of the protein is increased when the cell is contacted with the test compound, the increase being an indication that the test compound increases mitochondrial translocation of the protein. The protein can be any protein, e.g., a protein kinase such c-Abl or PKCd, that translocates to the mitochondria upon the induction of cellular stress.

In another aspect, the invention features a method of identifying a protein that is translocated to the mitochondria upon the induction of cellular stress. The method includes the steps of: providing a cell; subjecting the cell to a cellular stress; and identifying a protein that is translocated to the mitochondria of the cell. The protein can be any protein, e.g., a protein kinase, that translocates to the mitochondria upon the induction of cellular stress.

In one embodiment, the cellular stress includes oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

The step of detecting the mitochondrial translocation of the protein can include isolating the mitochondria of the cell and determining the presence or amount of the protein in the mitochondria as compared to the presence or amount of the protein in the mitochondria of a cell not subjected to the cellular stress. In one example, the method includes determining the amino acid sequence of all or a part of the protein.

In another aspect, the invention features a method of identifying a protein that interacts with a mitochondrial-translocated protein. The method includes the steps of: providing a cell; subjecting the cell to a cellular stress, wherein the cellular stress induces the mitochondrial translocation of a first protein; and identifying a second protein that binds to the first protein in the mitochondria upon the translocation of the first protein to the mitochondria. The first protein can be any protein, e.g., a protein kinase such as PKCd or c-Abl, that translocates to the mitochondria upon the induction of cellular stress.

In one embodiment, the cellular stress includes oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

The identifying step can include isolating the first protein and detecting the second protein bound to the first protein. For example, the method can include determining the amino acid sequence of all or a part of the second protein.

In another aspect, the invention features a method of identifying a compound that inhibits a protein-protein interaction. The method includes the steps of: providing a biological sample containing a first protein and a second protein, wherein the first protein is a protein that translocates to the mitochondria upon the induction cellular stress, and wherein the second protein interacts with the first protein when the first protein translocates to the mitochondria; contacting the biological sample with a test compound; and determining whether the first protein and the second protein interact in the presence of the test compound, wherein a decreased interaction between the first and second proteins in the presence of the test compound indicates that the compound inhibits the interaction. The first protein can be any protein, e.g., a protein kinase such as PKCd or c-Abl, that translocates to the mitochondria upon the induction of cellular stress.

In one embodiment, the cellular stress includes oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

In another aspect, the invention features a composition that binds to c-Abl or PKCd and inhibits cellular stress-induced mitochondrial translocation of c-Abl or PKCd.

The cellular stress can include oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

In another aspect, the invention features a composition that binds to c-Abl or PKCd and increases cellular stress-induced mitochondrial translocation of c-Abl or PKC.

The cellular stress can include oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

In another aspect, the invention features a method of inhibiting apoptosis of a cell, the method including inhibiting mitochondrial translocation of a protein in the cell. The protein can be any protein, e.g., a protein kinase such as PKCd or c-Abl, that translocates to the mitochondria upon the induction of cellular stress.

In one embodiment, the cellular stress includes oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

In another aspect, the invention features a method of increasing apoptosis of a cell, the method including increasing mitochondrial translocation of a protein in the cell. The protein can be any protein, e.g., a protein kinase such as PKCd or c-Abl, that translocates to the mitochondria upon the induction of cellular stress.

In one embodiment, the cellular stress includes oxidative stress. For example, a cell can be subjected to oxidative stress by contacting the cell with $H_2O_2$.

In another embodiment, the cellular stress includes ER stress. For example, a cell can be subjected to ER stress by administering a substance to the cell that increases intracellular calcium pools or blocks transport of proteins from the ER to Golgi.

In another embodiment, the cellular stress includes cytoskeletal stress.

In another embodiment, the cellular stress includes genotoxic stress.

In another aspect, the invention features a method of treatment. The method includes the following steps: selecting an individual suffering from or at risk of contracting a disorder associated with inappropriate levels of apoptosis; and administering to the individual a compound that modulates the mitochondrial translocation of c-Abl or PKCd. In one example, the disorder is characterized by excessive apoptosis, e.g., a neurological disorder. In another example, the disorder is characterized by insufficient apoptosis, e.g., cancer.

In another aspect, the invention features a method for identifying a compound that modulates (increases or decreases) binding of catalase to c-Abl or Arg, the method including: a) measuring binding of a first polypeptide containing catalase to a second polypeptide containing c-Abl or Arg in the presence of a test compound; and b) comparing the binding of the first polypeptide to the second polypeptide measured in step (a) to the binding of the first polypeptide to the second polypeptide in the absence of the test compound, wherein altered binding of the first polypeptide to the second polypeptide in the presence of the test compound compared the binding in the absence of the test compound indicates that the test compound modulates the binding of catalase to c-Abl or Arg.

The first polypeptide can optionally include only a fragment of catalase, e.g., human catalase, that binds to c-Abl or Arg. As described herein, c-Abl and Arg bind to the PFNP motif of catalase. Accordingly, the first polypeptide preferably contains the amino acid sequence PFNP. The first polypeptide can also include a fragment of catalase containing an amino acid residue, e.g., a tyrosine residue, that is phosphorylated by c-Abl and/or Arg. For example the first polypeptide can contain tyrosine 231 and/or tyrosine 386 of catalase.

The second polypeptide can optionally include only a fragment of c-Abl or Arg, e.g., human c-Abl or Arg, that binds to catalase. For example, the second polypeptide can include all or a portion of an SH3 domain of c-Abl or Arg that mediates binding to catalase.

The screening method can optionally include an additional step of measuring the binding of the first polypeptide to the second polypeptide in the absence of the test compound.

The screening method can be carried out in a cell-based system and/or in a cell-free system. For example, the binding of the first and second polypeptides can be measured in vitro using purified polypeptides in a cell free system. In addition, the ability of a test compound to modulate the binding of the first polypeptide to the second polypeptide can be measured on a living cell, using a cell-based system. In a cell based system, cells used in a screen can be recombinantly produced that express catalase, c-Abl, Arg, and/or a fragment of any of these proteins as described herein.

In another aspect, the invention features a method for identifying a modulator (activator or inhibitor) of catalase phosphorylation, the method including: a) contacting a first polypeptide containing catalase to a second polypeptide containing c-Abl or Arg in the presence of a test compound; b) measuring phosphorylation of the first polypeptide in the presence of the test compound, wherein altered phosphorylation of the first polypeptide in the presence of the test compound compared to the absence of the test compound indicates that the compound is a modulator of catalase phosphorylation.

The first polypeptide can optionally include only a fragment of catalase, e.g., human catalase, that is subject to phosphorylation by c-Abl or Arg. As described herein, c-Abl and Arg bind to the PFNP motif of catalase and phosphorylates tyrosine residue number 231 and tyrosine residue number 386 of catalase. Accordingly, the first polypeptide preferably contains the amino acid sequence PFNP. The first polypeptide can also include a fragment of catalase containing tyrosine 231 and/or tyrosine 386 of catalase.

The second polypeptide can optionally include only a fragment of c-Abl or Arg, e.g., human c-Abl or Arg, that phosphorylates catalase. For example, the second polypeptide can include all or a portion of a kinase domain of c-Abl or Arg that mediates phosphorylation of catalase. The second polypeptide can also include an SH3 domain of c-Abl or Arg that mediates binding to catalase.

The screening method can optionally include an additional step of measuring the phosphorylation of the first polypeptide in the absence of the test compound.

The screening method can be carried out in a cell-based system and/or in a cell-free system. For example, the phosphorylation of the first polypeptide can be measured in vitro using purified polypeptides in a cell free system. In addition, the ability of a test compound to modulate the phosphorylation of the first polypeptide can be measured on a living cell, using a cell-based system. In a cell based system, cells used in a screen can be recombinantly produced that express catalase, c-Abl, Arg, and/or a fragment of any of these proteins as described herein.

In another aspect, the invention features a method for identifying a modulator (activator or inhibitor) of catalase ubiquitination, the method including: a) contacting a polypeptide containing catalase to ubiquitin in the presence of a test compound; b) measuring the ubiquitination of the polypeptide in the presence of the test compound, wherein altered ubiquitination of the polypeptide in the presence of the test compound compared to the absence of the test compound indicates that the compound is a modulator of catalase ubiquitination.

The polypeptide can optionally include only a fragment of catalase, e.g., human catalase, that binds to ubiquitin. The polypeptide can also optionally include a fragment of catalase that binds to c-Abl or Arg and/or is subject to phosphorylation by c-Abl or Arg, as described herein.

The screening method can optionally include an additional step of measuring the ubiquitination of the polypeptide in the absence of the test compound.

The screening method can be carried out in a cell-based system and/or in a cell-free system. For example, the ubiquitination of the polypeptide can be measured in vitro using purified polypeptides in a cell free system. In addition, the ability of a test compound to modulate the ubiquitination of the polypeptide can be measured on a living cell, using a cell-based system. In a cell based system, cells used in a screen can be recombinantly produced that express catalase or a fragment thereof as described herein and optionally c-Abl, Arg, and/or a fragment of any of these proteins as described herein.

In another aspect, the invention features a method for identifying a modulator (activator or inhibitor) of catalase phosphorylation, the method including: a) contacting a polypeptide containing catalase to a test compound; b) measuring phosphorylation of the polypeptide in the presence of the test compound, wherein altered phosphorylation of the polypeptide in the presence of the test compound compared to the absence of the test compound indicates that the compound is a modulator of catalase phosphorylation.

The polypeptide can optionally include only a fragment of catalase, e.g., human catalase, that is subject to phosphorylation. For example, the first polypeptide can contain the amino acid sequence PFNP and/or a fragment of catalase containing tyrosine 231 and/or tyrosine 386 of catalase.

The screening method can optionally include an additional step of measuring the phosphorylation of the polypeptide in the absence of the test compound.

The screening method can be carried out in a cell-based system and/or in a cell-free system. For example, the phosphorylation of the polypeptide can be measured in vitro using purified polypeptides in a cell free system. In addition, the ability of a test compound to modulate the phosphorylation of the polypeptide can be measured on a living cell, using a cell-based system. In a cell based system, cells used in a screen can be recombinantly produced that express catalase or a fragment thereof as described herein and optionally c-Abl, Arg, and/or a fragment of any of these proteins as described herein.

In another aspect, the invention features a method of modulating (increasing or decreasing) apoptosis of a cell, the method including modulating the phoshorylation status of catalase in the cell.

In another aspect, the invention features a method of modulating (increasing or decreasing) apoptosis of a cell, the method including the ubiquitination status of catalase in the cell.

In another aspect, the invention features a method of treatment, the method including: selecting an individual suffering from or at risk of contracting a disorder associated with inappropriate levels of apoptosis; and administering to the individual an amount of a compound sufficient to modulate the phoshorylation status of catalase.

In another aspect, the invention features a method of treatment, the method including: selecting an individual suffering from or at risk of contracting a disorder associated with inappropriate levels of apoptosis; and administering to the individual an amount of a compound sufficient to modulate the ubiquitination status of catalase.

Unless otherwise defined; all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

The present invention provides methods of screening to identify compounds that modulate the ability of a protein to translocate to the mitochondria when a cell is subjected to cellular stress. Such compounds can be useful to modulate the level of apoptosis in a cell. For example, compounds identified according to the methods described herein can be used to treat disorders characterized by excessive apoptosis, e.g., a neurological disorder, or insufficient apoptosis, e.g., cancer.

As described in the accompanying Examples, mitochondrial signaling pathway has been identified that is activated in the response of a cell to cellular stress. For example, the protein kinases PKCd and c-Abl are shown to be activated by ROS exposure, target the mitochondria, and contribute to ROS-induced apoptosis. In this context, the blockade of these pathways results in a substantially complete abrogation of ROS-induced apoptosis (see Examples). By use of screening assays described herein, compounds can be identified that either inhibit or increase this mitochondrial translocation event and thereby inhibit or increase the level of apoptosis in a cell.

Methods of Screening

The present invention includes methods of screening to identify compounds that modulate (increase or decrease) the mitochondrial translocation of a protein, e.g., a protein kinase such as PKCd or c-Abl. In general, such compounds can be identified by subjecting a cell to a cellular stress that induces the mitochondrial translocation of a protein and determining whether a test compound is capable of modulating the mitochondrial translocation of the protein. Examples of cellular stress include oxidative stress, endoplasmic reticulum stress, cytoskeletal stress, and genotoxic stress.

Compounds that may be screened in accordance with the invention include, but are not limited to peptides, antibodies and fragments thereof, and other organic compounds that bind to a mitochondrial-translocated protein and modulate its activity, e.g., its ability to translocate to the mitochondria.

Examples of such compounds include: peptides such as soluble peptides, including members of random peptide libraries and combinatorial chemistry-derived molecular libraries made of D- and/or L configuration amino acids; phosphopeptides (e.g., members of random or partially degenerate, directed phosphopeptide libraries); antibodies (e.g., polyclonal, monoclonal, humanized, anti-idiotypic, chimeric or single chain antibodies, and FAb, F(ab')$_2$ and FAb expression library fragments, and epitope-binding fragments thereof); and small organic or inorganic molecules. Compounds that can be screened in accordance with the invention include small organic molecules that are able to gain entry into an appropriate cell and affect the ability of a protein, e.g., PKCd or c-Abl, to translocate to the mitochondria.

Computer modeling and searching technologies can be used to assist in the identification of compounds that can modulate the ability of a protein to translocate to the mitochondria. The active site of a compound can be identified using methods known in the art including, for example, the study of complexes of the relevant compound or composition with its ligand, e.g., PKCd or c-Abl.

In general, the screening methods described herein entail the detection of the presence or the amount of a protein, e.g., PKCd or c-Abl, in the mitochondria of a cell subjected to a particular cellular stress. The presence or amount of the protein in the mitochondria, as compared to an untreated cell, is indicative of the protein's translocation to the mitochondria. This mitochondrial translocation event can be detected by a variety of methods well known to those of skill in the art. For example, a particular protein to be analyzed, e.g., PKCd or c-Abl, can be linked to a detectable marker, e.g., green fluorescent protein, and the presence of the detectable marker in the mitochondria can be used an indication of the presence protein in the mitochondria. In addition, cellular components can be separated and the mitochondria can be analyzed for the presence or amount of a particular protein. Thus, according to these methods, the ability of a protein to translocate to the mitochondria in the presence of a test compound can be evaluated.

Compounds identified via methods described herein may be useful, for example, for the treatment of disorders associated with inappropriate levels of apoptosis or aberrant activity or expression of a mitochondrial-translocated protein.

Identification of Molecules that Interact with Mitochondrial-Translocated Proteins The invention features methods for identifying molecules that can associate with mitochondrial-translocated proteins. The mitochondrial-translocated protein can be any protein translocated to the mitochondria in response to a cellular stress, e.g., a cellular stress as described herein. Examples of mitochondrial-translocated proteins include protein kinases such as c-Abl and PKCd.

Any method that is suitable for detecting an interaction, e.g., a protein-protein interaction, between two molecules can be employed to detect a molecule that associates with a mitochondrial-translocated protein. For example, the method includes identifying a protein, e.g., a naturally occurring protein, that interacts with a mitochondrial-translocated protein when the mitochondrial-translocated protein is translocated to the mitochondria. Among the traditional methods that can be employed are co-immunoprecipitation, crosslinking, and co-purification through gradients or chromatographic columns of cell lysates or proteins obtained from cell lysates and the use of the mitochondrial-translocated protein to identify proteins in the lysate that interact with the mitochondrial-translocated protein. For these assays, the mitochondrial-translocated protein can be a full length or a fragment of the protein, e.g., a fragment containing a catalytic domain such as a kinase domain. A protein associated with a mitochondrial translocated protein can be identified by, for example, use of two dimensional gel analysis and/or mass spectrometry (e.g., a technique such as Matrix Assisted Laser Desorption/Ionization (MALDI) mass analysis). For example, proteins that bind to the mitochondrial-translocated protein and are selectively detected by gel electrophoresis after the cell is subjected to cellular stress constitute candidates for sequencing by mass spectrometry methods. Once isolated, such an interacting protein can be identified and cloned and then used, in conjunction with standard techniques, to alter the activity of the mitochondrial-translocated protein with which it interacts. For example, the interacting protein can be used in a screening assay of a type described herein to identify a compound that modulates the protein-protein interaction and thus modulates the apoptotic pathway.

Identification of Mitochondrial-Translocated Molecules

The present application describes a variety of pathways that involve the translocation of proteins to the mitochondria following the treatment of a cell with a cellular stress. This identification of the mitochondria as a site of protein translocation as a part of the apoptotic program permits the use of the organelle to screen for additional molecules (including proteins as well as any other molecules) that translocate, either in or out, of the mitochondria in response to cellular stress. Such molecules constitute important targets for the generation of compounds that modulate apoptosis.

Mitochondrial-translocated molecules can be identified by using methods similar to those of other screening assays described herein. For example, the mitochondrial protein content of a cell subjected to a cellular stress can be compared to the mitochondrial protein content a cell not subjected to the stress. A protein that is detected as preferentially translocating into or out of the mitochondria in response to a cellular stress constitutes a candidate for further characterization. For example, a mitochondrial-translocated protein can be initially identified by two dimensional gel electrophoresis (e.g., as a protein present in the mitochondria of stressed cells but not in control cells) and then further characterized by mass spectrometry (e.g., by MALDI mass analysis).

Profiling of proteins and/or other molecules (such as co-factors or metabolites) in the mitochondria pre and post stress induction, e.g., oxidative stress induction, can provide comprehensive understanding of translocations in and out of the mitochondria under stress conditions. Such profiling screens can be performed in any cell type, e.g., tumor cell lines or neuronal cell lines. Stress inducing agents include those that induce oxidative stress, endoplasmic reticulum stress, cytoskeletal stress, and genotoxic stress.

Methods of Treatment

As described herein, modulating (increasing or decreasing) the mitochondrial translocation of a protein such as c-Abl or PKCd can be used to treat an individual suffering from or at risk of contracting a disorder associated with inappropriate levels of apoptosis. Compositions useful for modulating mitochondrial translocation of c-Abl or PKCd are described herein.

Certain disorders are associated with an increased number of surviving cells that are produced and continue to survive or proliferate when apoptosis is inhibited. These disorders include, for example, cancer (particularly follicular lymphomas, carcinomas associated with mutations in p53, and hormone-dependent tumors such as breast cancer, prostate cancer, and ovarian cancer), autoimmune disorders (such as systemic lupus erythematosis, immune-mediated glomerulonephritis), and viral infections (such as those caused by herpesviruses, poxviruses, and adenoviruses). For example, failure to remove autoimmune cells that arise during development or that develop as a result of somatic mutation during an immune response can result in autoimmune disease.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Pharmaceutical Compositions

Compounds that modulate the mitochondrial translocation of a protein such as c-Abl or PKCd are expected to be useful in modulating the cell death that is associated with this translocation event. Methods of identifying a variety of compounds that modulate mitochondrial translocation of a protein are described herein. These compounds can be used to treat disorders characterized by excessive or insufficient apoptosis.

Pharmaceutical compositions for use in accordance with the present invention can be formulated in a conventional manner using one or more physiologically acceptable carriers or excipients. Thus, the compounds and their physiologically acceptable salts and solvates may be formulated for administration by inhalation, insufflation (either through the mouth or the nose), oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form for constitution with a suitable vehicle, for example, sterile pyrogen-free water, before use.

The compounds can also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (e.g., subcutaneously or intramuscularly) or by intramuscular injection. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The therapeutic compositions of the invention can also contain a carrier or excipient, many of which are known to persons of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol.

EXAMPLES

Example 1

Activation of the Cytoplasmic c-Abl Tyrosine Kinase by Reactive Oxygen Species Cell Culture:

COS7 cells and mouse embryonic fibroblasts (MEFs) derived from wild-type and c-Abl$^{-/-}$ mice were cultured in Dulbecco's modified Eagle's medium containing 10% heat-inactivated fetal calf serum, 2 mM L-glutamine, 100 units/ml penicillin and 100 μg/ml streptomycin. DLD1 cells were grown as described (Polyak et al. (1997) *Nature* 389, 300–305). Cells were treated with H$_2$O$_2$ (Sigma), 30 mM N-acetyl-L-cysteine (NAC; Sigma) or 10 μM cis-platinum (Sigma).

Analysis of Kinase Activity:

Cell lysates were prepared in lysis buffer (10 mM Tris-HCl, pH 7.5, 10 mM NaCl, 1 mM DTT, 0.1 mM EDTA, 3 mM MgCl$_2$, 0.5 mM PMSF, 5 μg/ml leupeptin) containing 0.5% Nonidet P-40 and subjected to immunoprecipitation as described (Kharbanda et al. (1997) *Nature* 386, 732–735) with anti-c-Abl (sc-23; Santa Cruz) or mouse IgG (Santa Cruz). The immunoprecipitates were resuspended in kinase buffer (20 mM HEPES, pH 7.4, 10 mM MgCl$_2$, 10 mM MnCl$_2$) containing 2.5 μCi [g-32P]ATP and GST-Crk (120–225) or GST-Crk(120–212) for 20 minutes at 30° C. Anti-PKCd (sc-937; Santa Cruz) and anti-ERK1 (sc-93; Santa Cruz) immunoprecipitates were analyzed by using histone H1 and myelin basic protein (Upstate Biotecnology Inc.), respectively, as substrates. The reaction products were analyzed by SDS-PAGE and autoradiography.

Isolation of Cytoplasmic and Nuclear Fractions:

Cells were disrupted in lysis buffer containing 0.05% NP-40. The cytoplasmic and nuclear fractions were prepared as described (Kharbanda et al. (1996) *Cancer Res.* 56, 3617–3621).

Preparation of Cytoplasts:

Enucleated cells were prepared by density centrifugation as described (Gudas et al. (1986) *J. Cell. Physiol.* 128, 441–448). Cells were incubated in 21 μM cytochalasin B for 1 hour at 37° C., layered over a discontinuous Ficoll gradient and centrifuged at 80,000× g for 1 hour. Cytoplasts were collected at the 12.5–15% Ficoll interface. Cytoplast purity was assessed by staining with 0.5 mg/ml 4',6-diamino-2-phenylindole (DAPI) and was greater than 95% free of whole cells.

Immunoblot Analysis:

Proteins were separated by SDS-PAGE, transferred to nitrocellulose and probed with anti-c-Abl, anti-IkBα (sc-847; Santa Cruz) or anti-cytochrome c (Kirken et al. (1995) *Protein Expression & Purification* 6, 707–715). The antigen-antibody complexes were visualized by enhanced chemiluminescence (ECL; Amersham).

Apoptosis Assays:

DNA content was assessed by staining ethanol-fixed cells with propidium iodide and monitoring by FACScan (Becton-Dickinson).

Results and Discussion:

To determine whether c-Abl is activated by ROS, lysates from COS7 cells exposed to H$_2$O$_2$ were subjected to immunoprecipitation with mouse IgG, as a control, or anti-c-Abl antibody. The precipitates were assayed for phosphorylation of a GST-Crk(120–225) fusion protein (Feller et al. (1994) *EMBO J.* 13, 2341–2351; Ren et al. (1994) *Genes Dev.* 8, 783–795). There was no detectable phosphorylation of GST-Crk(120–225) with the control immunoprecipitates. A low level of GST-Crk(120–225) phosphorylation was detectable when assaying anti-c-Abl immunoprecipitates from control cells, whereas exposure to H$_2$O$_2$ resulted in stimulation (4–5 fold) of the Crk kinase activity. By contrast, there was no detectable H$_2$O$_2$-induced phosphorylation of a GST-Crk (120–212) fusion protein that lacks the c-Abl phosphorylation site at Y-221. The results also show that H$_2$O$_2$ treatment is not associated with increases in the level of c-Abl protein. To confirm involvement of ROS in c-Abl activation, cells were treated with N-acetylcysteine (NAC), a scavenger of reactive oxygen intermediates and precursor of glutathione (Roederer et al. (1990) *Proc. Natl. Acad. Sci.* (*U.S.A.*). 87, 4884–4888; Staal et al. (1990) *Proc. Natl. Acad. Sci.* (*U.S.A.*). 87, 9943–9947). NAC treatment inhibited H$_2$O$_2$-induced phosphorylation of GST-Crk(120–225) by c-Abl. The induction of c-Abl activity was dependent on H$_2$O$_2$ concentration, with increases of 5-fold upon exposure to 1 mM. In addition, maximal induction of c-Abl activity was observed at 30–60 minutes. The finding that human DLD1 cells respond to H$_2$O$_2$ with activation of c-Abl further indicated that the results are not restricted to certain cell types.

To extend the analysis of H$_2$O$_2$-induced activation of c-Abl to other pathways involved in the ROS response, mouse embryo fibroblasts null for c-Abl expression were studied (c-Abl–/– MEFs) (Tybulewicz et al. (1991) *Cell* 65, 1153–1163). There was no detectable c-Abl activity is control or H$_2$O$_2$-treated c-Abl$^{-/-}$ cells. By contrast, wild-type MEFs responded to H$_2$O$_2$ with induction of c-Abl activity. Recent studies have demonstrated that c-Abl interacts with PKCd in the response to oxidative stress (Sun et al. (2000) *J. Biol. Chem.* 275, 7470–7473). To determine whether c-Abl is required for activation of PKCd, we assayed anti-PKCd immunoprecipitates from c-Abl$^{-/-}$ and wild-type MEFs. The results demonstrate that, while PKCd is required for activation of c-Abl, c-Abl is dispensable for activation of PKCd in the ROS response. Other studies have demonstrated that ERK1 is activated in cells exposed to H$_2$O$_2$ (Guyton et al. (1996) *J. Biol. Chem.* 271, 4138–4142). Analysis of anti-ERK1 immunoprecipitates from H$_2$O$_2$-treated c-Abl$^{-/-}$ and wild-type MEFs demonstrated activation of ERK1 by a c-Abl-independent mechanism. These findings demonstrate that activation of c-Abl in the ROS response is not functional in the induction of PKCd or ERK1 activities.

As nuclear c-Abl is activated in the stress response to DNA damage (Kharbanda et al. (1995) *Nature* 376, 785–788), studies were performed to define the subcellular localization of ROS-induced c-Abl activation. Cells were treated with H$_2$O$_2$ before preparation of nuclear and cytoplasmic fractions. Analysis of cytoplasmic anti-c-Abl immunoprecipitates demonstrated increased phosphorylation of GST-Crk(120–225). By contrast, there was no detectable activation of c-Abl in the nuclear fraction. Oxygen radicals induce lesions in nuclear DNA (Imlay et al. (1988) *Science* 240, 1302–1309; Imlay et al. (1988) *Science* 240, 640–642) and nuclear c-Abl is activated by DNA damage (Kharbanda et al. (1995) *Nature* 376, 785–788). To determine whether a nuclear signal is required for H$_2$O$_2$-induced activation of cytoplasmic c-Abl, cytoplasts devoid of nuclei were assayed. Treatment of the cytoplasts with H$_2$O$_2$ was associated with induction of c-Abl activity. By contrast, cisplatin treatment, which activates nuclear c-Abl, had no detectable effect on c-Abl activity in cytoplasts. These findings indicate that cytoplasmic c-Abl is activated in the response to oxidative stress by a mechanism independent of nuclear signals.

The cellular response to genotoxic stress includes release of mitochondrial cytochrome c and the induction of apoptosis (Kharbanda et al. (1997) *Proc. Natl. Acad. Sci. USA* 94, 6939–6942). To determine whether oxidative stress induces cytochrome c release, cytoplasmic lysates from wild-type and c-Abl$^{-/-}$ cells treated with $H_2O_2$ were subjected to immunoblotting with anti-cytochrome c. The results demonstrate that $H_2O_2$ treatment of wild-type MEFs is associated with increased levels of cytochrome c. By contrast, cytochrome c release was not detectable in c-Abl$^{-/-}$ MEFs treated with $H_2O_2$. To determine whether c-Abl contributes to the induction of apoptosis by oxidative stress, $H_2O_2$-treated MEFs were assayed for the appearance of sub-G1 DNA. The results demonstrate that, compared to wild-type MEFs, the c-Abl$^{-/-}$ MEFs exhibit an attenuated apoptotic response to $H_2O_2$ exposure. Analysis at 3 to 24 h of $H_2O_2$ exposure confirmed that cells deficient in c-Abl expression exhibit a defective apoptotic response. The finding that $H_2O_2$-induced release of cytochrome c is completely abrogated in c-Abl$^{-/-}$ cells indicates that the attenuated induction of apoptosis in response to $H_2O_2$ is mediated by signals by a cytochrome c-independent pathway. These results collectively demonstrate that cytoplasmic $H_2O_2$ induces cytochrome c release and apoptosis by a c-Abl-dependent mechanism.

Oxidative cellular damage contributes to ageing (Migliaccio et al. (1999) *Nature* 402, 309–313) and, in the presence of acute ROS exposure, the induction of apoptosis (Buttke et al. (1994) *Immunol Today* 15, 7–10). Previous work has shown that the nuclear c-Abl kinase is activated in the apoptotic response of cells to genotoxic stress (see, e.g., Yuan et al. (1999) *Nature* 399, 814–817). Conversely, the present studies demonstrate that cytoplasmic, and not nuclear, c-Abl is activated in the apoptotic response to oxidative stress. Whereas DNA damage-induced apoptosis is mediated by activation of c-Abl and the release of mitochondrial cytochrome c (Kharbanda et al. (1997) *Proc. Natl. Acad. Sci. USA* 94, 6939–6942), less is known about involvement of mitochondrial signals in $H_2O_2$-induced cell death. The present results demonstrate that cytochrome c release is also induced in response to oxidative stress and that this event is c-Abl dependent. These findings support a model in which c-Abl functions in determining cell fate by conferring stress-induced signals to the release of cytochrome c and thereby apoptosis. The findings further indicate that the subcellular distribution of c-Abl determines localization of the specific response to apparently diverse environmental stresses. The present findings demonstrate that, analogous to activation of nuclear c-Abl by DNA damaging agents, cytoplasmic c-Abl is activated by ROS-induced stress.

Example 2

Mitochondrial Translocation of Protein Kinase C Delta in Phorbol Ester-Induced Cytochrome C Release and Apoptosis Cell Culture and Reagents:

Human U-937 myeloid leukemia cells (ATCC, Rockville, Md.) were grown in RPMI 1640 medium supplemented with 10% heat-inactivated fetal bovine serum (FBS), 100 units/ml penicillin, 100 µg/ml streptomycin, and 2 mM L-glutamine. MCF-7, MCF-7/neo, MCF-7/PKCdRD and 293T cells were grown in Dulbecco's modified Eagle's medium (DMEM) containing 10% FBS. Cells ($3 \times 10^6/150$ mm culture dish) were plated 24 hours before treating with 250 nM TPA (Sigma Chemical Co.), 100 nM bryostatin 1 (ICN, Ohio), 10 µM 1,2-dioctanoyl-sn-glycerol (DOG; Calbiochem) and 0.5 units/ml phospholipase C (PLC; Sigma). Cells were also treated with 10 µM rottlerin (Calbiochem).

Isolation of Mitochondria:

Cells were washed twice with phosphate buffer saline (PBS), homogenized in buffer A (210 mM manitol, 70 mM sucrose, 5 mM HEPES, 1 mM EGTA) and 110 ug/ul digitonin in a glass homogenizer (Pyrex no. 7727-07) and centrifuged at 5000 g for 20 min. Pellets were resuspended in buffer A, homogenized in a small glass homogenizer (Pyrex no. 7726) and centrifuged at 2000 g for 5 minutes. Supernatant (S1) was collected and the pellet again homogenized in of buffer A. Supernatant (S2) was collected after centrifugation at 2000 g for 5 minutes. Supernatants S1 and S2 were mixed and centrifuged at 11000 g for 10 min. Mitochondrial pellets were disrupted in lysis buffer at 4° C. for 30 minutes and then centrifuged at 15000 g for 20 minutes. The concentration of mitochondrial proteins in the supernatant was determined using Bio-Rad protein estimation kit.

Isolation of the Cytosolic Fraction:

Cells were washed twice with PBS and the pellet was suspended in 5 ml of ice-cold buffer B containing 250 mM sucrose. The cells were homogenized by disrupting three times in a Dounce homogenizer in buffer B (20 mM HEPES, pH 7.5, 1.5 mM $MgCl_2$, 10 mM KCl, 1 mM EDTA, 1 mM EGTA, 1 mM DTT, 0.1 mM PMSF and 10 µg/ml leupeptin and aprotinin). After centrifugation for 5 min at 4° C., the supernatants then were centrifuged at 105,000× g for 30 minutes at 4° C. The resulting supernatant was used as the soluble cytosolic fraction.

Immunoprecipitation and Immunoblot Analysis:

Total, cytoplasmic or mitochondrial lysates were subjected to immunoprecipitation with anti-GFP, anti-PKCγ (Santa Cruz Biotechnology, Calif.), anti-PKCµ (Santa Cruz), anti-PKCζ (UBI), anti-PKCθ (Santa Cruz), anti-PKCε (Santa Cruz), anti-PKCε (Santa Cruz) or anti-PKCd (Santa Cruz) antibodies. Proteins were separated by SDS-PAGE and transferred to nitrocellulose membranes. The residual binding sites were blocked by incubating the filters with 5% nonfat dry milk in PBST (PBS/0.05% Tween 20). The filters were incubated with anti-PKCd, anti-cytochrome c (22), anti-Hsp-60 (Stressgen, Canada), anti-Actin (Sigma), anti-PKCγ, anti-PKCµ, anti-PKCζ or anti-GFP (Clontech, Palo Alto, Calif.). After washing twice with PBST, the filters were incubated with anti-rabbit or anti-mouse IgG peroxidase conjugate and developed by ECL (Amersham).

Plasmids:

pEGFP-PKCd and PKCd-RD were prepared as described (Kumar et al. (2000) *EMBO J.* 19, 1087–1097). The pEGFP-PKCd(K378R) was generated by site-directed mutagenesis (Sun et al. (2000) *J. Biol. Chem.* 275, 7470–7473).

Transient Transfections:

293T cells were transiently transfected with empty vector (pEGFP-C1), GFP-PKCd or pEGFPCy-PKCd (K378R) using SuperFect (Qiagen). At 24 hours after transfection, cells were lysed in lysis buffer (50 mM Tris, pH 7.4, 150 mM NaCl, 1% Nonidet P-40, 1 mM sodium vanadate, 1 mM phenylmethylsulfonyl fluoride, 1 mM dithiothreitol, and 10 µg/ml leupeptin and aprotinin) and subjected to immunoblotting with anti-PKCd and anti-GFP. Signal intensities were determined by densitometric analysis.

Immunofluorescence Microscopy:

Cells immobilized on slides were fixed with 3.7% formaldehyde, permeabilized with 0.2% Triton X-100, incubated with 20 ng anti-PKCd/slide and then Texas Red-conjugated goat anti-rabbit IgG (Southern Biotechnology Associates, Inc). Mitochondria were stained with 0.006 ng/slide of Mitotracker Green FM (Molecular Probes). The slides were analyzed using a Zeiss Auxiphot fluorescence microscope coupled to a CCD camera and a power Macintosh 8100. Image analysis was performed using the IPLab Spectrum 3.1 software (Signal Analytics).

PKCd Activity Assays:

293T cells were transiently transfected with GFP-PKCd or GFP-PKCd(K-R). Total cell lysates were subjected to immunoprecipitation with anti-PKCd, anti-PKCθ, anti-PKCε, anti-PKCη, anti-PKCμ or anti-PKCζ. The immune complex kinase assays were performed using H1 histone as a substrate as described (Bharti et al. (1998) $Mol.$ $Cell.$ $Biol.$ 18, 6719–6728).

Quantitation of Apoptosis by Flow Cytometric Analysis:

Cells were harvested, washed twice with PBS and fixed with 80% ethanol. Cells ($10^6$ cells/ml) were washed and incubated with propidium iodide (2.5 mg/ml) and RNase (50 mg/ml). FACScan (Becton Dickinson) was used to assess cells with sub-GI DNA content.

Results and Discussion:

To determine whether PKC regulates mitochondrial function, human U-937 cells were treated with TPA to activate PKC. PKC translocation was assessed by subjecting cytoplasmic and mitochondrial fractions to immunoblotting with anti-PKC antibodies. The results demonstrate that TPA treatment is associated with decreases in cytoplasmic PKCd and concomitant increases in mitochondrial PKCd. As controls, the cytoplasmic and mitochondrial fractions were also subjected to immunoblotting with anti-actin and anti-Hsp60 to ensure purity of the preparations. By contrast to translocation of PKCd, TPA had no detectable effect on cytoplasmic or mitochondrial levels of PKCγ and PKCζ. The immunoblots were scanned to calculate percent PKCd translocation to mitochondria. The results demonstrate that approximately 40% of PKCd translocates to mitochondria in response to TPA.

The demonstration that PKCd also translocates to mitochondria in TPA-treated MCF-7 cells indicates that the finding is not restricted to certain cell types. In addition, to confirm the subcellular redistribution of PKCd in TPA-treated cells, intracellular fluorescence was visualized with a CCD camera and image analyzer. Examination of fluorescence markers in control cells showed distinct patterns for anti-PKCd (red signal) and a mitochondrion-selective dye (Mitotracker; green signal). The demonstration that TPA induces a marked change in fluorescence signals (red and green→yellow/orange) supported translocation of PKCd to mitochondria. These findings obtained by immunofluorescence microscopy thus confirm the results of PKCd redistribution found by subcellular fractionation.

To determine whether the natural product bryostatin, which activates PKC (Stone et al. (1988) $Blood$ 72, 208–213), also induces the translocation of PKCd, mitochondrial lysates from U-937 cells treated with 100 nM bryostatin were subjected to immunoblot analysis with anti-PKCd. As a control, mitochondrial lysates were also subjected to immunoblot analysis with anti-PKCζ. The results demonstrate that, in contrast to PKCζ, treatment with bryostatin was associated with translocation of PKCd to mitochondria. Phospholipase C (PLC) is activated by cell membrane-initiated signaling pathways and, by conferring the hydrolysis of phosphatidylinositol or phosphatidylcholine, results in the formation of DAG. To determine whether PLC induces the translocation of PKCd, mitochondrial lysates from U-937 cells treated with 0.5 units/ml PLC were subjected to immunoblot analysis with anti-PKCd. The results demonstrate that, treatment with PLC is associated with translocation of PKCd to mitochondria. To confirm the involvement of DAG in mitochondrial translocation of PKCd, cells were treated with a cell permeable DAG (DOG). Immunoblot analysis of DOG-treated cell lysates demonstrated that DOG induced the translocation of PKCd to mitochondria. These findings indicate that, like TPA, treatment with byostatin, PLC and DOG is associated with redistribution of cytosolic PKCd to mitochondria.

To determine whether activation of PKCd is required for translocation to mitochondria, cells were transfected with a vector expressing green fluorescence protein (GFP)-tagged PKCd. Immunoblot analysis with anti-GFP demonstrated no detectable PKCd in the mitochondrial fraction from cells transfected with an empty GFP vector. By contrast, transfection of kinase-active CFP PKCd was associated with PKCd expression in mitochondria. Moreover, treatment of the GFP-PKCd-transfected cells with TPA resulted in further increases in levels of mitochondrial PKCd. Significantly, transfection of kinase-inactive GFP-PKCd(K-R) had no effect on expression of mitochondrial PKCd. In addition, overexpression of GFP-PKCd(K-R) blocked the TPA-induced translocation of PKCd to mitochondria. To demonstrate that PKCd(K-R) specifically blocks endogenous PKCd activity, and not that other isoforms of PKC, 293T cells were transiently transfected with GFP-PKCd or GFP-PKCd(K-R). Following transfection, cell lysates were subjected to immunoprecipitation with anti-PKCd, anti-PKCμ, anti-PKCζ, anti-PKCθ, anti-PKCη or anti-PKCε. The precipitates were assayed in in vitro kinase assays using H1 histone as substrate. The results demonstrate that, in contrast to PKCμ, PKCζ, PKCθ or PKCη, overexpression of PKCd (K-R) specifically inhibits the activity of endogenous PKCd. The results also indicate that overexpression of PKCd(K-R) is associated with slight inhibition of the phosphorylated and active PKCε. PKCd consists of an N-terminal regulatory domain (RD) and a C-terminal catalytically active fragment (CF) (Ghayur et al. (1996) $J.$ $Exp.$ $Med.$ 184, 2399–2404). MCF-7 cells stably transfected to express the 35 kDa RD exhibit attenuation of TPA-induced PKCd activity. Translocation of PKCd to mitochondria was also attenuated in TPA-treated MCF-7/PKCdRD cells as compared to that in MCF-7 cells expressing the empty neo vector. Other studies were performed with rottlerin, a selective inhibitor of PKCd activation. Treatment of U-937 cells with rottlerin abrogated TPA-induced localization of PKCd to mitochondria. These findings collectively demonstrate that PKCd activation is necessary for its translocation to mitochondria.

The potential role of PKCd translocation was explored by assessing mitochondrial release of cytochrome c. Whereas diverse apoptotic signals induce cytochrome c release, phorbol ester treatment of cells has not been associated with this event. Immunoblot analysis of cytoplasmic fractions with anti-cytochrome c demonstrated that TPA treatment of U-937 cells is associated with cytochrome c release. Similar results were obtained when U-937 cells were treated with PLC or DOG. To determine whether PKCd functions in inducing cytochrome c release, U-937 cells were pretreated with rottlerin before adding TPA. Of note, treatment of cells with rottlerin alone is associated with cytotoxic effects that contribute to a detectable release of cytochrome c. By contrast, analysis of cytoplasmic lysates demonstrated that rottlerin significantly blocks TPA-induced cytochrome c release. As these findings indicate that the PKCd kinase function is required for TPA-induced release of cytochrome c, 293T cells were transfected to express GFP, GFP-PKCd or GFP-PKCd(K-R) and then treated with TPA. Immunoblotting of the cytoplasmic fraction from GFP positive cells demonstrated abrogation of TPA-induced cytochrome c release in cells expressing PKCd(K-R) compared to that in cells transfected with the GFP-PKCd vector. Taken together, these results and those obtained for PKCd translocation support a role for PKCd in the mitochondrial release of cytochrome c.

The release of cytochrome c from mitochondria triggers activation of caspases and induction of apoptosis (Liu et al. (1996) *Cell* 86, 147–157). To determine whether TPA-induced PKCd translocation and thereby cytochrome c release contributes to apoptosis, U-937 cells treated with rottlerin and TPA were assayed for sub-G1 DNA content. The results demonstrate that treatment with rottlerin alone induces a low level of apoptosis. By contrast, the apoptotic response of U-937 cells to TPA was significantly attenuated by inhibition of PKCd with rottlerin. Moreover, treatment of MCF-7/neo cells with TPA was also associated with the induction of apoptosis. By contrast, the apoptotic response to TPA was significantly attenuated in MCF-7/PKCdRD cells. Taken together with the other findings, these results support a role for TPA-induced localization of PKCd to mitochondria and in the induction of apoptosis.

Previous work has demonstrated that TPA treatment is associated with translocation of PKCd to the cell membrane (Ohmori et al. (1998) *Mol. cell. Biol.* 18, 5263–5271). The present studies demonstrate that TPA treatment of diverse cell types is associated with translocation of PKCd to mitochondria. These findings have been confirmed by cell fractionation and immunofluorescence studies. The results further demonstrate that the PKCd kinase function is necessary for TPA-induced mitochondrial localization. The functional significance of PKCd translocation to mitochondria is supported by the finding that this event is linked to mitochondrial release of cytochrome c. Moreover, the results demonstrate that abrogation of PKCd translocation to mitochondria significantly inhibits TPA-induced apoptosis. These findings thus support a model in which TPA induces the release of cytochrome c and thereby apoptosis by a PKCd-dependent mechanism.

Example 3

Targeting of Protein Kinase C d to Mitochondria in the Oxidative Stress Response Cell culture and reagents: Human U-937 myeloid leukemia cells (ATCC, Manassas, Va.) were maintained in RPMI 1640 medium containing 10% heat-inactivated fetal bovine serum (FBS), 100 units/ml penicillin, 100 mg/ml streptomycin and 2 mM L-glutamine. Human MCF-7, MCF-7/neo and MCF-7/PKCdRD (15) breast cancer cells, 293T cells and wild-type and c-Abl$^{-/-}$ MEFs (Tybulewicz et al. (1991) *Cell* 65, 1153–1163) were grown in Dulbecco's modified Eagle's medium containing 10% FBS and antibiotics. Cells were treated with 1 mM $H_2O_2$ (Sigma Chemical Co.), 10 mM rottlerin (Sigma) and 30 mM N-acetyl-L-cysteine (NAC; Calbiochem). Transfections were performed with Superfect (Qiagen).

Isolation of the Cytosolic Fraction:

Cells were suspended in ice-cold 20 mM HEPES, pH 7.5, 1.5 mM Mg $Cl_2$, 10 mM KCl, 1 mM EDTA, 1 mM EGTA, 1 mM dithiothreitol (DTT), 0.1 mM phenylmethylsulphonyl fluoride (PMSF), 10 mg/ml leupeptin, 10 mg/ml aprotinin, 10 mg/ml pepstatin A and 250 mM sucrose. The cells were disrupted by Douce homogenization. After centrifugation at 1500× g for 5 minutes at 4° C., the supernatants were then centrifuged at 105,000× g for 30 minutes at 4° C. The resulting supernatant was used as the soluble cytoplasmic fraction.

Isolation of the Mitochondrial Fraction:

Cells were suspended in ice-cold 5 mM HEPES, pH 7.5, 210 mM mannitol, 1 mM EGTA, 70 mM sucrose and 110 mg/ml digitonin. The cells were disrupted in a glass homogenizer (Pyrex No. 7727-07) and centrifuged at 2000× g for 20 minutes at 4° C. The pellets were resuspended in the same buffer, homogenized again (Pyrex No. 7726) and centrifuged at 2000× g for 5 minutes at 4° C. The supernatants (S1) were collected. The pellets were re-homogenized, centrifuged at 2000× g for 5 minutes and the resultant supernatants (S2) collected. Supernatants S1 and S2 were pooled and centrifuged at 11,000× g for 10 minutes. The mitochondrial pellets were resuspended in lysis buffer (50 mM Tris-HCl, pH 7.4, 150 mM NaCl, 1% NonidetxP-40, 1 mM sodium vanadate, 1 mM PMSF, 1 mM DTT, 10 mg/ml leupeptin and 10 mg/ml aprotinin) for 30 minutes on ice and then centrifuged at 15,000× g for 20 minutes. The supernatant was used as the soluble mitochondrial fraction. Protein concentration was determined by the BioRad protein estimation kit.

Immunoblot Analysis:

Soluble proteins were subjected to immunoblot analysis with anti-PKCd (Santa Cruz Biotechnology), anti-b-actin (Sigma), anti-Hsp60 (Stressgen), anti-IkBα (Santa Cruz), anti-PKCζ (Santa Cruz), anti-PKCγ (Santa Cruz), anti-GFP (Clontech) and anti-cytochrome c (Kirken et al. Prot. Exp. Purif. 6: 707–715, 1995). The immune complexes were detected with anti-rabbit or anti-mouse IgG peroxidase conjugate (Amersham) and visualized by ECL chemiluminescence (Amersham Pharmacia).

Immunofluorescence Microscopy:

Cells immobilized on slides were fixed with 3.7% formaldehyde, permeabilized with 0.2% Triton X-100, incubated with 20 ng of anti-PKCd/slide and then Texas Red-conjugated goat anti-rabbit IgG (Southern Biotechnology Associates). Mitochondria were stained with 0.006 ng/slide of Mitotracker Green FM (Molecular Probes). The slides were analyzed with a Zeiss Auxiphot fluorescence microscope coupled to a CCD camera and a power Macintosh 8100. Image analysis was performed using the IPLab Spectrum 3.1 software (Signal Analytics).

Assessment of PKCd Activity:

PKCd activity was assayed by incubating anti-PKCd immunoprecipitates in PKC kinase buffer containing 20 mM Tris-HCl, pH 7.5, 10 mM Mg $Cl_2$, 20 mM ATP, 2.5 mCi [g-32P]ATP and 200 mg/ml histone H1 for 5 minutes at 30° C. The reaction products were analyzed by SDS-PAGE and autoradiography.

Assessment of Apoptosis:

Cells were fixed with 80% ethanol, washed, and incubated with 2.5 mg/ml propidium iodide and 50 mg/ml RNase. Cells with sub-G1 DNA were determined by FACScan (Becton Dickinson).

Results and Discussion:

To assess the effects of ROS on subcellular distribution of PKCd, human U-937 cells were treated with $H_2O_2$ and harvested at varying intervals. Cytoplasmic and mitochondrial fractions were subjected to immunoblotting with anti-PKCd. The results demonstrate that treatment with 1 mM $H_2O_2$ is associated with decreases in cytoplasmic and concomitant increases in mitochondrial PKCd. The finding that treatment with higher concentrations of $H_2O_2$ is associated with increased localization of PKCd to mitochondria indicated that this response is dose-dependent. Immunoblot analysis of the fractions with antibodies against cytosolic b-actin and mitochondrial Hsp60 was performed to assure purity of the preparations. In contrast to the response of PKCd to $H_2O_2$ treatment, there was little if any effect of this agent on mitochondrial levels of PKCζ or PKCγ. To confirm involvement of ROS in targeting of PKCd to mitochondria, cells were treated with NAC, a scavenger of reactive oxygen intermediates and precursor of glutathione. The results demonstrate that NAC inhibits $H_2O_2$-induced localization of PKCd to mitochondria. To extend these findings, intracellular localization of PKCd was visualized with a CCD camera and image analyzer. Fluorescence detection in control cells showed distinct patterns for PKCd (red signal) and a mitochondrial-selective dye (Mitotracker; green signal). The finding that $H_2O_2$ treatment is associated with a change in fluorescence signals (red and green→yellow/orange) provided further support for translocation of PKCd to mitochondria.

To determine whether PKCd activity contributes to mitochondrial targeting of PKCd in response to $H_2O_2$, NIH3T3 cells were treated with the selective PKCd inhibitor, rottlerin. As found in U-937 cells, treatment with $H_2O_2$ was associated with localization of PKCd to mitochondria. Moreover, the demonstration that rotterlin inhibits $H_2O_2$-induced translocation of PKCd to mitochondria supported involvement of the PKCd kinase function. Other studies have demonstrated that PKCd interacts with the c-Abl tyrosine kinase in the cellular response to oxidative stress (Sun et al. (2000) *J. Biol. Chem.* 275, 7470–7473). To determine whether c-Abl is necessary for $H_2O_2$-induced targeting of PKCd to mitochondria, wild-type and c-Abl$^{-/-}$ MEFs were treated with $H_2O_2$. $H_2O_2$-induced activation of PKCd was similar in both cells. In addition, localization of PKCd to mitochondria was detectable in the response of both wild-type and c-Abl$^{-/-}$ cells. To extend this analysis, cells were transfected with vectors expressing GFP, GFP-PKCd or a kinase-inactive GFP-PKCd(K378R) mutant (Sun et al. (2000) *J. Biol. Chem.* 275, 7470–7473). Analysis of the mitochondrial fraction by immunoblotting with anti-GFP demonstrated $H_2O_2$-induced targeting of PKCd to mitochondria. By contrast, $H_2O_2$ had no apparent effect on mitochondrial localization of GFP-PKCd (K378R). These findings indicate that activation of the PKCd kinase function is necessary for $H_2O_2$-induced mitochondrial localization.

Example 1 demonstrates that treatment of COS cells with $H_2O_2$ is associated with cytochrome c release. The finding that $H_2O_2$ also induces cytochrome c release in U-937 cells indicated that this response is not restricted by cell type. To determine whether PKCd is functional in inducing the release of cytochrome c, U-937 cells were pretreated with NAC or rottlerin. The results demonstrate that NAC blocks $H_2O_2$-induced release of cytochrome c. Importantly, pretreatment with rottlerin also blocked the release of cytochrome c in response to $H_2O_2$ treatment. To extend these findings, 293 cells were transfected with GFP, GFP-PKCd or GFP-PKCd(K-R) and then treated with $H_2O_2$. Analysis of cytoplasmic lysates demonstrated that transfection of GFP-PKCd is associated with release of cytochrome c and that this effect is stimulated by $H_2O_2$ treatment. By contrast, expression of GFP-PKCd(K378R) had no detectable effect on cytochrome c release and blocked the response to $H_2O_2$. These results and those obtained for translocation of PKCd to mitochondria support the involvement of PKCd in $H_2O_2$ induced release of cytochrome c.

PKCd consists of an N-terminal regulatory domain (RD) and a C-terminal catalytic fragment. To further assess the role of PKCd in $H_2O_2$-induced cytochrome c release and apoptosis, we studied MCF-7 cells that stably express the empty neo vector (MCF-7/neo) or the 35 kDa RD (MCF-7/PKCdRD) (see description of constructs in Example 2). In contrast to MCF-7/neo cells, translocation of PKCd to mitochondria was attenuated in $H_2O_2$-treated MCF-7 cells stably expressing PKCdRD. The release of cytochrome c in response to $H_2O_2$ was also attenuated in MCF-7/PKCdRD, as compared to MCF-7/neo, cells. In concert with these results, $H_2O_2$ treatment of MCF-7/neo cells was associated with the induction of apoptosis and this response was attenuated in the MCF-7/PKCdRD cells. These findings demonstrate that targeting of PKCd to mitochondria contributes to $H_2O_2$-induced cytochrome c release and apoptosis.

ROS have been implicated in the regulation of both cell growth and apoptosis. Although the signals activated by ROS are for the most part unclear, previous work has demonstrated that PKCd is phosphorylated on tyrosine in the cellular response to $H_2O_2$ treatment (see, e.g., Konishi et al. (1997) *Proc. Natl. Acad. Sci. USA.* 94, 11223–11237). Other studies have shown that c-Abl interacts with PKCd and is in part responsible for tyrosine phosphorylation of PKCd in the response to $H_2O_2$ (Sun et al. (2000) *J. Biol. Chem.* 275, 7470–7473). The available findings indicate that PKCd is activated by ROS and that PKCd phosphorylates and activates c-Abl. In a potential auto-catalytic loop, c-Abl phosphorylates and further activates PKCd. The present studies demonstrate that ROS induce targeting of PKCd to mitochondria and that this response is dependent on activation of the PKCd kinase function. The results also demonstrate that ROS-induced targeting of PKCd to mitochondria occurs in c-Abl$^{-/-}$ cells. These findings indicate that, while c-Abl activation is dependent on PKCd, activation and translocation of PKCd to mitochondria in the response to $H_2O_2$ is independent of the c-Abl kinase.

The results of the present studies show that ROS-induced cytochrome c release is regulated by activation and translocation of PKCd to mitochondria. Taken together with the demonstration that c-Abl functions in the apoptotic response to oxidative stress, these findings indicate that signaling by both PKCd and c-Abl is needed for ROS-induced release of cytochrome c. Indeed, while treatment of c-Abl$^{-/-}$ cells with $H_2O_2$ is associated with PKCd activation and localization to mitochondria, these cells failed to respond to oxidative stress with release of cytochrome c and induction of apoptosis. Finally, PKCd is also activated by PDK1-mediated phosphorylation in the cellular response to serum stimulation (Le Good et al. (1998) *Science* 281, 2042–2045). Thus, PKCd appears to be functional in both pro and anti-apoptotic pathways and therefore could represent a switch that determines cell fate.

Example 4

Targeting of the c-Abl Tyrosine Kinase to Mitochondria in the Necrotic Cell Death Response to Oxidative Stress Cell Culture:

Human U-937 myeloid leukemia cells (ATCC, Manassas, Va.) were grown in RPMI 1640 medium supplemented with 10% heat-inactivated fetal bovine serum (FBS), 100 units/ml penicillin, 100 mg/ml streptomycin and 2 mM L-glutamine. Wild-type, c-Abl$^{-/-}$ and c-Abl+ MEFs, MCF-7, MCF-7/c-Abl(K-R), SH-SY5Y (neuroblastoma) and 293T cells were maintained in Dulbecco's modified Eagle's medium containing 10% FBS and antibiotics. Cells were treated with 1 mM $H_2O_2$ (Sigma) and 30 mM N-acetyl-L-cysteine (NAC; Sigma). Transient transfections were performed in the presence of calcium phosphate.

Immunofluorescence Microscopy:

Cells were plated onto poly D-lysine coated glass coverslips 1 day prior to $H_2O_2$ treatment (1 hour) and then fixed with 3.7% formaldehyde/PBS (pH 7.4) for 10 minutes. Cells were washed with PBS, permeabilized with 0.2% Triton X-100 for 10 minutes washed again and incubated for 30 minutes in complete medium. The coverslips were then incubated with 5 mg/ml of anti-c-Abl (K-12) for 1 hour followed by Texas Red-goat anti-rabbit Ig (H+L) conjugate (Molecular Probes, Eugene, Oreg.). Mitochondria were stained with 100 nM Mitotracker Green FM (Molecular Probes, OR). Nuclei were stained with 4,6-diamino-2-phenylindole (DAPI; 1 mg/ml in PBS). Coverslips were mounted onto slides with 0.1 M Tris (pH 7.0) in 50% glycerol. Cells were visualized by digital confocal immunofluorescence and images were captured with a cooled CCD camera mounted on a Zeiss Axioplan 2 microscope. Images were deconvolved using Slidebook software (Intelligent Imaging Innovations, Inc., Denver, Colo.).

Isolation of Mitochondria:

Cells ($3 \times 10^6$) were washed twice with PBS, homogenized in buffer A (210 mM mannitol, 70 mM sucrose, 1 mM EGTA, 5 mM HEPES, pH 7.4) and 110 mg/ml digitonin in a glass homogenizer (Pyrex no. 7727-07) and centrifuged at $5000 \times$ g for 20 minutes. Pellets were resuspended in buffer A, homogenized in a small glass homogenizer (Pyrex no. 7726) and centrifuged at $2000 \times$ g for 5 minutes. The supernatant was collected and centrifuged at $11,000 \times$ g for 10 minutes. Mitochondrial pellets were disrupted in lysis buffer (20 mM Tris-HCl, pH 7.5, 150 mM NaCl, 1% NP-40, 1 mM DTT, 1 mM sodium orthovanadate, 1 mM PMSF, 10 mM sodium fluoride, 10 mg/ml leupeptin and aprotinin) at 4° C. and then centrifuged at $15,000 \times$ g for 15 minutes. Protein concentration was determined by the Bio-Rad protein estimation kit.

Preparation of Cell Lysates:

Whole cell lysates (WCL) were prepared as described (Kharbanda et al. (1995) *Nature* 376, 785–788) and analyzed for protein concentration.

Immunoprecipitation and Immunoblot Analysis.

Soluble proteins (100 mg) were incubated with anti-c-Abl (K-12; Santa Cruz Biotechnology) for 1 hour and precipitated with protein A-sepharose for 30 minutes. Immunoprecipitates and lysates (5 mg) were resolved by SDS-PAGE and analyzed by immunoblotting with anti-c-Abl (24–11; Santa Cruz), anti-HSP60 (Stressgen, Victoria, British Columbia), anti-b-actin (Sigma) anti-PCNA (Calbiochem), anti-PDGF receptor (Oncogene) and anti-PKCd (Santa Cruz).

Analysis of Mitochondrial Membrane Potential:

Cells were incubated with 50 ng/ml Rhodamine 123 (Molecular Probes) for 15 minutes at 37° C. After washing with PBS, samples were analyzed by flow cytometry using 488 nm excitation and the measurement of emission through a 575/26 (ethidium) bandpass filter.

Quantitation of ATP:

ATP levels were measured using an ATP Determination Kit (Molecular Probes).

Assessment of Apoptosis and Necrosis by Flow Cytometry:

Cells were analyzed by staining with annexin-V-fluorescein and propidium iodide (Annexin-V-FLOUS staining kit; Roche Diagnostics). Samples were analyzed by flow cytometry (Becton Dickinson) using 488 nm excitation and a 515 nm bandpass filter for fluorescein detection and a >600 nm filter for propidium iodide (PI) detection.

Results and Discussion:

To assess the effects of ROS on c-Abl, the subcellular localization of c-Abl in response to $H_2O_2$ was investigates by measuring intracellular fluorescence with a high sensitivity CCD camera and image analyzer. Examination of the distribution of fluorescence markers in control MEFs showed distinct patterns for anti-c-Abl (red signal) and a mitochondrion-selective dye (Mitotracker; green signal). By contrast, exposure to $H_2O_2$ was associated with a marked change in fluorescence signals (red and green→yellow/orange) supporting translocation of c-Abl to mitochondria. To confirm targeting of c-Abl to mitochondria in the response to ROS, mitochondria were isolated from MEFs treated with $H_2O_2$. Analysis of the mitochondrial fraction by immunoblotting with antic-Abl demonstrated an increase in c-Abl protein that was detectable at 30 minutes and through 3 hours. Densitometric scanning of the signals demonstrated over a 5-fold increase in c-Abl protein at 0.5 to 1 hour of $H_2O_2$ treatment. Immunoblotting for the mitochondrial HSP60 protein was used to assess loading of the lanes. Moreover, purity of the mitochondrial fraction was confirmed by reprobing the blots with antibodies against the cytoplasmic b-actin protein, the nuclear PCNA protein and the cell membrane PDGF receptor. To estimate the amount of c-Abl protein that localizes to mitochondria, whole cell and mitochondrial lysates, each prepared from $3 \times 10^6$ cells, were subjected to immunoblotting with anti-c-Abl. Densitometric scanning of the signals and adjustment for lysate volume indicated that mitochondrial c-Abl is approximately 4% of the total cellular c-Abl protein. Following treatment with $H_2O_2$, approximately 20% of total c-Abl localizes to mitochondria. As an additional control, mitochondrial lysates were first subjected to immunoprecipitation with anti-c-Abl. Immunoblot analysis of the immunoprecipitates with anti-c-Abl showed $H_2O_2$-induced increases in levels of mitochondrial c-Abl protein. The demonstration that c-Abl levels are increased in the mitochondria of $H_2O_2$-treated human U-937 leukemia cells and human neuroblastoma cells further indicated that this response occurs in diverse cell types.

To confirm involvement of ROS in targeting of c-Abl to mitochondria, MEFs were treated with NAC, a scavenger of reactive oxygen intermediates and precursor of glutathione. NAC treatment inhibited $H_2O_2$-induced translocation of c-Abl to mitochondria. Also to determine whether ROS-induced activation of the c-Abl kinase function is necessary for targeting of c-Abl to mitochondria, MCF-7 cells stably expressing a kinase-inactive c-Abl(K-R) mutant at levels comparable that of kinase-active c-Abl in MCF-7/neo cells were treated with $H_2O_2$. The finding that MCF-7/neo, but not MCF-7/c-Abl(K-R), cells respond to $H_2O_2$ with translocation of c-Abl to mitochondria supported a requirement for the c-Abl kinase function. These results indicate that ROS-induced c-Abl activation is associated with the targeting of c-Abl to mitochondria.

As described in the examples above, ROS appears to activate c-Abl by a mechanism dependent on the PKCd kinase. To determine whether PKCd contributes to mitochondrial targeting of c-Abl, MEFs were treated with the selective PKCd inhibitor, rottlerin. While rottlerin had no effect on constitutive levels of mitochondrial c-Abl, this agent inhibited $H_2O_2$-induced c-Abl translocation. To extend the interaction of PKCd and c-Abl, 293 cells were cotransfected with HA-c-Abl and PKCd. Analysis of the mitochondrial fraction by immunoblotting with anti-HA demonstrated targeting of HA-c-Abl to mitochondria is increased by $H_2O_2$ treatment. By contrast, cotransfection of HA-c-Abl and kinase-inactive PKCd was associated with less targeting of c-Abl to mitochondria and no apparent effect of $H_2O_2$ treatment. These findings provide support for the involvement of ROS-induced activation of PKCd in mitochondrial targeting of c-Abl.

To determine whether c-Abl is necessary for ROS-induced loss of mitochondrial transmembrane potential ($\Psi$), wild-type and c-Abl$^{-/-}$ cells were treated with $H_2O_2$ and then stained with Rhodamine 123. Mitochondrial transmembrane potential was substantially diminished in $H_2O_2$-treated wild-type cells. By contrast, the $\Psi$ was protected from ROS-induced loss in c-Abl$^{-/-}$ cells, but not in c-Abl$^{-/-}$ cells transfected to stably express c-Abl (c-Abl+). Cyclosporin A prevents the reduction in $\Psi$ induced by various agents that open mitochondrial permeability transition pores. In this context, pretreatment of wild-type MEFs with cyclosporin A (100 mM for 1 hour) abrogated the $H_2O_2$-induced change in T. Both apoptosis and necrosis are associated with decreases in $\Psi$, while necrosis is distinguished from apoptosis by depletion of ATP and an early loss of plasma membrane integrity. To assess the involvement of c-Abl in ROS-induced necrosis, wild-type, c-Abl$^{-/-}$ and c-Abl+ cells were treated with $H_2O_2$ and assayed for ATP levels. The results demonstrate that, while $H_2O_2$ treatment of wild-type and c-Abl+ cells is associated with depletion of ATP, this response was attenuated in c-Abl$^{-/-}$ cells. As these findings support the involvement of c-Abl in a necrotic-like cell death, cells were stained with both annexin-V and PI to assess plasma membrane integrity. The results demonstrate that, compared to wild-type and c-Abl+ MEFs, loss of plasma membrane integrity in response to $H_2O_2$ is attenuated in c-Abl$^{-/-}$ cells. These findings demonstrate that ROS-induced targeting of c-Abl to mitochondria is associated with loss of mitochondrial membrane potential, ATP depletion and necrotic cell death.

Activation of the c-Abl kinase in the cellular response to oxidative stress is dependent on PKCd and associated with release of mitochondrial cytochrome c. These findings provided support for involvement of c-Abl in the regulation of mitochondrial signaling. The present studies demonstrate that ROS target the c-Abl protein to mitochondria and that this response is dependent on the c-Abl kinase function. Moreover, in concert with the demonstration that PKCd is required for ROS-induced activation of c-Abl, PKCd was shown to be necessary for targeting of c-Abl to mitochondria. Importantly, localization of c-Abl to mitochondria is associated with loss of the mitochondrial transmembrane potential. Apoptosis and necrosis both involve loss of mitochondrial membrane potential, while depletion of ATP is found selectively in necrosis. Thus, the demonstration that mitochondrial targeting of c-Abl is associated with depletion of ATP indicated that c-Abl is functional in necrotic-like cell death. In this context, wild-type, but not c-Abl$^{-/-}$, MEFs also responded to oxidative stress with dysfunction of the plasma membrane. These findings and the previous demonstration that c-Abl is involved in ROS-induced cytochrome c release (Example 1) indicate that targeting of c-Abl to mitochondria confers both pro-apoptotic and pro-necrotic cell death signals.

Example 5

Targeting of the c-Abl Tyrosine Kinase to Mitochondria in ER Stress-Induced Apoptosis Cell Culture:

Rat1 cells and MEFs derived from wild-type and c-Abl$^{-/-}$ mice were cultured in Dulbecco's modified Eagle's medium containing 10% heat-inactivated fetal calf serum, 2 mM L-glutamine, 100 units/ml penicillin and 100 mg/ml streptomycin. Cells were treated with A23187 (Sigma) or Brefeldin A (Sigma).

Digital Confocal Immunofluorescence Microscopy:

Cells grown on poly-D-lysine coated glass coverslips were fixed (3.7% formaldehyde in PBS, pH 7.4; 10 minutes), permeabilized (0.2% Triton X-100; 10 min), blocked for 30 minutes in media containing serum. After rinsing with PBS, immunostaining was performed by incubating the cells with 50 ng/slide of anti-c-Abl (K-12 rabbit polyclonal; Santa Cruz) and anti-grp-78 (C-20 goat polyclonal; Santa Cruz). For c-Abl and calreticulin staining, cells were incubated first with anti-c-Abl alone for 1 hour followed by blocking for 30 minutes in media containing serum. After washing with PBS, cells were then incubated with anti-calreticulin (rabbit polyclonal; StressGen). Finally, cells were incubated with a 1:250 dilution of CY-3 or Fluorescein (FITC)-conjugated anti-rabbit or anti-goat secondary antibodies (Jackson ImmunoResearch) for 1 hour. Mitochondria were stained with 0.006 ng/slide Mitotracker Green FM (Molecular Probes). Nuclei were stained with 4,6-diamino-2-phenylindole (DAPI; 1 mg/ml in PBS). Coverslips were mounted onto slides with 0.1 M Tris (pH 7.0) in 50% glycerol. Cells were visualized by digital confocal immunofluorescence and images were captured with cooled CCD camera mounted on a Zeiss Axioplan 2 microscope. Images were deconvolved using Slidebook software (Intelligent Imaging Innovations, Inc., Denver, Colo.).

Immnuo-Electronemicroscopic Analysis:

Cells were fixed with 2% paraformaldehyde in 0.1 M sodium cacodylate buffer for 10 minutes, washed with three changes of cacodylate buffer, postfixed with 1% osmium tetroxide for 5 minutes, dehydrated in graded ethanol, and infiltrated and polymerized with Poly/bed 812 overnight. Ultrathin sections were cut with an ultramicrotome Nova (Leica). After etching with sodium periodate for 10 minutes, the sections were rinsed with buffer and incubated with anti-c-Abl at a dilution of 1:10 overnight at 4° C. The sections were rinsed with buffer, incubated with protein A gold (15 nm) for 1 hour, rinsed again, and then fixed with 2% glutaradehyde in PBS for 2 minutes. After air drying, the sections were stained with 25 aqueous uranyl acetate and with 0.5% lead citrate. The sections were examined and photographed using a Hitachi H-600 electron microscope (Nessei Sagnyo) at 75 KV.

Isolation of the ER Fraction:

Cells were washed with PBS, lysed in homogenization buffer (50 mM Tris-HCl, pH 8.0, 1 mM b-mercaptoethanol, 1 mM EDTA, 0.32 M sucrose and 0.1 mM PMSF), and then centrifuged at 5,000× g for 10 minutes. The supernatant was collected and centrifuged at 105,000× g for 1 hour. The pellet was disrupted in lysis buffer (50 mM Tris-HCl, pH 7.5, 150 mM NaCl, 1% NP-40, 1 mM DTT, 1 mM sodium orthovanadate, 1 mM PMSF, 10 mM sodium fluoride, 10 mg/ml leuptin and aprotinin) at 4° C. and then centrifuged at 15,000× g for 20 minutes. The resulting supernatant was used as the ER fraction.

Isolation of Cytoplasmic and Nuclear Fractions:

The cytoplasmic and nuclear fractions were isolated as described in Example 1.

Isolation of Mitochondria:

Cells were washed twice with PBS, homogenized in buffer A (210 mM mannitol, 70 mM sucrose, 1 mM EGTA, 5 mM HEPES, pH 7.4) with 110 mg/ml digitonin in a glass homogenizer (Pyrex no. 7727-07) and then centrifuged at 5000× g for 5 minutes. Pellets were resuspended in buffer A, homogenized in a glass homogenizer and centrifuged at 1500× g for 5 minutes. The supernatant was collected and centrifuged at 10,000× g for 10 minutes. Mitochondrial pellets were disrupted in lysis buffer at 4° C. and then centrifuged at 15,000× g for 20 minutes. Protein concentration was determined by the Bio-Rad protein estimation kit.

Immunoblot analysis: Proteins were separated by SDS-PAGE, transferred to nitrocellulose and probed with anti-c-Abl (Calbiochem), anti-grp78 (Santa Cruz), anti-calreticulin (StressGen), anti-HSP60 (StressGen), anti-b-actin (Sigma), anti-PCNA (Calbiochem) or anti-cytochrome c. Antigen-antibody complexes were visualized by enhanced chemiluminescence (ECL; Amersham Pharmacia Biotech).

Analysis of c-Abl Activity:

Cell lysates were prepared as described in Example 1 and subjected to immunoprecipitation with anti-c-Abl (K-12; Santa Cruz). The immunoprecipitates were resuspended in kinase buffer (see Example 1) containing 2.5 mCi of [g-32P] ATP and GST-Crk(120–225) or GST-Crk(120–212) for 15 minutes at 30° C. The reaction products were analyzed by SDS-PAGE and autoradiography.

Apoptosis Assays:

DNA content was assessed by staining ethanol-fixed cells with propidium iodide and monitoring by FACScan (Becton-Dickinson).

Localization of c-Abl to the ER:

To assess the subcellular distribution of c-Abl, confocal microscopy was performed to detect colocalization of c-Abl with proteins that are selectively expressed in different organelles. Using an antibody against the ER protein grp78, the distribution of immunofluorescence was compared to that obtained with anti-c-Abl. Colocalization of grp78 (green) and c-Abl (red) was supported by overlay of the signals (red+green→yellow/orange). Similar results were obtained in colocalization studies of c-Abl and the ER protein calreticulin. Immunogold labeling of cells with anti-c-Abl showed expression of c-Abl in the cytoplasm, mitochondria and rough ER. These findings indicate that c-Abl localizes to the ER.

Subcellular fractionation studies were performed to define the fraction of c-Abl that associates with the ER. To assess intracellular distribution of ER, cytosolic and mitochondrial fractions were subjected to immunoblotting with anti-c-Abl. Analysis of equal amounts of proteins from the fractions indicated that the concentration of c-Abl in the ER is higher than that found in the cytosol or mitochondria. The purity of the ER fraction was confirmed by immunoblotting with antibodies against calreticulin, b-actin and HSP60. Thus, the ER fraction included calreticulin, and little if any cytosolic b-actin or mitochondrial HSP60. Analysis of c-Abl protein in the different fractions, including the nucleus, indicated that c-Abl localized to the ER comprises about 20% of c-Abl protein in the total cell lysate.

ER Stress Decreases ER-Associated c-Abl:

To assess whether ER stress affects the subcellular localization of c-Abl, ER fractions were isolated from cells treated with A23187. Immunoblot analysis demonstrated that A23187 treatment is associated with a time-dependent decrease in c-Abl levels. As shown previously, ER stress induced by A23187 was associated with increases in expression of grp78. Equal loading of the lanes was confirmed by immunoblotting with anti-calreticulin. ER fractions isolated from cells treated with Brefeldin A to inhibit transport of protein from the ER to Golgi were also subjected to immunoblotting with anti-c-Abl. The results demonstrate that Brefeldin A, like A23187, decreases c-Abl expression in the ER. Brefeldin A treatment was also associated with increases in grp78 and had little if any effect on levels of calreticulin. These findings demonstrate that ER stress downregulates localization of c-Abl to the ER.

ER Stress Targets c-Abl to Mitochondria:

The subcellular relocalization of c-Abl in response to ER stress was investigated by measuring intracellular fluorescence. Examination of the distribution of fluorescence markers in control cells showed distinct patterns for anti-c-Abl (red signal) and a mitochondrion-selective dye (Mitotracker: green signal). By contrast, treatment with A23187 was associated with a change in fluorescence signals (red and green→yellow/orange) supporting translocation of c-Abl to mitochondria. Similar results were obtained with Brefeldin A-treated cells. By contrast, there was little if any change in expression of c-Abl in the cytoplasm or nucleus. These results indicate that ER stress-induced downregulation of c-Abl in the ER is associated with targeting of c-Abl to mitochondria.

ER Stress Activates the c-Abl Kinase:

To further define the distribution of c-Abl in response to ER stress, cytoplasmic and nuclear fractions from A23187-treated cells were assessed by immunoblot analysis with anti-c-Abl. The results demonstrate that A23187 has little if any effect on c-Abl levels in the cytoplasm or nucleus. Purity of the fractions was confirmed by immunoblotting with anti-b-actin, anti-PCNA and anti-calreticulin. In contrast to the cytoplasm and nucleus, immunoblot analysis of the mitochondrial fraction from A23187-treated cells demonstrated a time-dependent increase in c-Abl protein.

The mitochondrial fraction was also subjected to immunoprecipitation with antic-Abl. Analysis of the immunoprecipitates for phosphorylation of GST-Crk(120–225) demonstrated that A23187 treatment is associated with increases in mitochondrial c-Abl activity. As a control, there was no detectable phosphorylation of GST-Crk(120–212) that lacks the c-Abl Y-221 phosphorylation site. Densitometric scanning of the signals obtained for phosphorylation of GST-Crk(120–225) as compared to those obtained for immunoprecipitated c-Abl protein indicated that A23187 induces c-Abl activity.

Targeting of c-Abl to mitochondria was similarly assessed in cells treated with Brefeldin A. Immunoblot analysis of the cytoplasmic and nuclear fractions showed no detectable effect of Brefeldin A on c-Abl levels. As found with A23187, analysis of the mitochondrial fraction demonstrated Brefeldin A-induced increases in c-Abl protein. In addition, Brefeldin A treatment was associated with increases in mitochondrial c-Abl activity. Comparison of the signals found for GST-Crk(120–212) phosphorylation and c-Abl protein indicated that Brefeldin A induces activation of the c-Abl kinase. These findings and those obtained with A23187 demonstrate that ER stress is associated with targeting of c-Abl to mitochondria and stimulation of c-Abl activity.

ER Stress Induces Cytochrome c Release and Apoptosis by a c-Abl-Dependent Mechanism:

To assess the functional significance of ER stress-induced targeting of c-Abl to mitochondria, wild-type and c-Abl$^{-/-}$ MEFs were treated with A23187. Immunoblot analysis of the mitochondrial fraction demonstrated A23187-induced increases in mitochondrial c-Abl levels in wild-type, but not c-Abl$^{-/-}$, cells. Cytoplasmic fractions were also subjected to immunoblot analysis to assess release of mitochondrial cytochrome c. The results demonstrate that A23187 induces the release of cytochrome c in wild-type, but not c-Abl$^{-/-}$, MEFs. Similar results were obtained in wild-type and c-Abl$^{-/-}$ cells treated with Brefeldin A. In concert with these findings, A23187 treatment was associated with the induction of sub-G1 DNA in wild-type cells, but had little effect on the induction of apoptosis in c-Abl$^{-/-}$ cells. The finding that ER stress-induced apoptosis is also abrogated in c-Abl$^{-/-}$ MEFs treated with Brefeldin A provided further support for involvement of c-Abl in this response. These results demonstrate that ER stress induces cytochrome c release and apoptosis by a c-Abl-dependent mechanism.

Stress Signaling from the ER to Mitochondria:

The ER responds to alterations in homeostasis with the transduction of signals to the nucleus and cytoplasm. In this context, eukaryotic cells respond to the accumulation of unfolded or excess proteins in the ER with i) transcriptional activation of genes encoding ER-resident proteins, and ii) repression of protein synthesis. The ER-resident transmembrane kinases, IRE1α/IRE1β, are activated by the presence of incorrectly folded proteins within the ER lumen and transduce signals that induce JNK/SAPK activity and gene transcription (see, e.g., Shamu et al. (1996) EMBO J. 15, 3028–3039). Inhibition of protein synthesis in the response to unfolded proteins is signaled by the PERK transmembrane ER-resident kinase (Harding et al. (1999) Nature 397, 271–274). PERK has a lumenal domain similar to that of IRE1 and a cytoplasmic kinase domain that phosphorylates eIF2α. ER stress responses are also activated by disruption of ER calcium homeostasis. The calcium ionophore A23187 induces ER stress by increasing intracellular calcium pools. Brefeldin A, by contrast, induces ER stress by blocking transport of proteins from the ER to Golgi. Under conditions of excessive ER stress, cells activate signaling pathways that induce apoptosis. However, the mechanisms responsible for ER stress-induced apoptosis have been largely unknown. The results of the present studies demonstrate that the ER responds to diverse types of stress with the transduction of signals to mitochondria and thereby the induction of apoptosis.

c-Abl Confers ER Stress Signals to Mitochondria:

The available evidence has shown that c-Abl is expressed in the nucleus and cytoplasm. The present results demonstrate that c-Abl also localizes to the ER. Confocal microscopy studies demonstrate that c-Abl colocalizes with the ER-associated grp78 and calreticulin proteins. Localization of c-Abl to the ER was confirmed by immuno-electron microscopy and subcellular fractionation studies. Nuclear c-Abl is activated in the cellular response to genotoxic stress by mechanisms dependent on DNA-PK and ATM. Cytoplasmic c-Abl is activated in the response to oxidative stress by a PKCd-dependent mechanism (see, e.g., Example 1). The finding, as described in Example 1, that c-Abl is required for the release of cytochrome c in the oxidative stress response has further supported a role for c-Abl in targeting pro-apoptotic signals to mitochondria. The present studies extend the link between c-Abl and cellular stress by demonstrating that ER stress is associated with mitochondrial targeting of c-Abl. The results support a model in which ER stress induces translocation of the ER-associated c-Abl to mitochondria. The results also support a functional role for c-Abl in transducing pro-apoptotic signals that are activated by ER stress.

ER Stress Induces Cytochrome c Release and Apoptosis by Targeting c-Abl to Mitochondria:

In the cytosol, cytochrome c associates with a complex of Apaf-1 and caspase-9, and thereby induces the activation of caspase-3 (see, e.g., Li et al. (1997) Cell 91, 479–489). The induction of apoptosis is associated with caspase-3-mediated cleavage of poly(ADP-ribose) polymerase (PARP), PKCd and other proteins. While ER stress can induce apoptosis, the involvement of cytochrome c release in this response has been unknown. In the present studies, the finding that ER stress induces the release of mitochondrial cytochrome c provided further support for signaling from the ER to mitochondria. Importantly, the induction of cytochrome c release by ER stress was attenuated in c-Abl$^{-/-}$ cells. Moreover, c-Abl$^{-/-}$ cells were defective in the apoptotic response to ER stress. These findings indicate that ER stress-induced cytochrome c release and apoptosis are mediated by targeting c-Abl from the ER to mitochondria.

Example 6

Proteosome Degradation of Catalase is Regulated by the C-ABL and ARG Tyrosine Kinases c-Abl and Arg Regulate Catalase Stability:

To determine whether c-Abl and/or Arg regulates catalase expression, lysates from wild-type, c-abl–/– and arg–/– MEFs were analyzed by immunoblotting with an anti-catalase antibody. The results demonstrated little if any effect of c-Abl or Arg deficiency on catalase levels. By contrast, catalase expression was increased 2–3-fold in c-abl–/–arg–/– cells. The finding that similar results were obtained in separate clones of c-abl–/–arg–/– cells indicated that the increase in catalase expression was not due to clonal variation.

To confirm that the absence of Arg is associated with increases in catalase, the c-abl–/–arg–/– cells were transduced with a retrovirus expressing Arg. Compared to c-abl–/–arg–/– cells expressing the empty vector, Arg expression was associated with decreased levels of catalase.

Catalase mRNA levels were found to be similar in wild-type MEFs and c-abl–/–arg–/– cells, indicating that catalase is regulated by stability of the protein. To assess the half-life of catalase, MEFs and c-abl–/–arg–/– cells were treated with CHX and then monitored for catalase levels. The results demonstrated a catalase half-life of approximately 10.5 hours in MEFs and greater than 24 hours in c-abl–/–arg–/– cells. To confirm the effects of c-Abl and Arg on catalase stability, 293 cells were transfected to express Flag-catalase and c-Abl or Arg. Cotransfection of Flag-catalase and the empty vector resulted in a half-life of greater than 9 hours. By contrast, the half-life of catalase was less than 3 hours when co-expressed with c-Abl or Arg. These findings demonstrate that the stability of catalase is regulated by c-Abl and Arg.

Ubiquitination of Catalase by a c-Abl/Arg-Mediated Mechanism:

To determine if catalase is subject to ubiquitination, catalase was incubated in an in vitro ubiquitination system. Analysis of reaction products by immunoblotting with an anti-catalase antibody demonstrated reactivity over a range of electrophoretic mobilities. In concert with these findings, immunoblotting with an anti-ubiquitin (Ub) antibody demonstrated ubiquitination of catalase.

To determine if catalase is regulated by the Ub-proteosome pathway, anti-catalase antibody immunoprecipitates from wild-type MEFs were analyzed by immunoblotting with an anti-Ub antibody. The results showed anti-Ub reactivity over a range of electrophoretic mobilities. By contrast, similar studies in c-abl−/−arg−/− cells demonstrated a substantial decrease in anti-Ub reactivity. As a control, immunoprecipitation of catalase was found to be comparable from the wild-type MEFs and c-abl−/−arg−/− cells. In the reciprocal experiment, anti-Ub immunoprecipitates analyzed by immunoblotting with an anti-catalase antibody demonstrated a higher level of ubiquitinated catalase in MEFs as compared to c-abl−/−arg−/− cells. Studies of c-abl−/− and arg−/− cells also demonstrated higher levels of ubiquitinated catalase. These results demonstrate that catalase is ubiquitinated by a c-Abl/Arg-dependent mechanism.

Degradation of Catalase by the 26S Proteosome:

In studies using an in vitro Ub-proteosome system, catalase was found to be subject to proteosomal degradation. As a control, degradation was inhibited when [g-S]ATP was substituted for ATP to prevent ubiquitination. Degradation of catalase was also blocked when the proteosome inhibitor, MG132, was added to the reaction. Lactacystin, another proteosome inhibitor, was used to assess degradation of catalase in cells. Treatment of wild-type MEFs with lactacystin was associated with an increase in catalase levels. Lactacystin treatment of c-abl−/−arg−/− cells, however, had little if any effect.

In 293 cells expressing Flag-catalase and c-Abl, lactacystin increased the half-life of catalase. Similar results were obtained with lactacystin when Flag-catalase was coexpressed with Arg. MG132 also increased the half-life of catalase in cells. These findings indicate that c-Abl and Arg target catalase for ubiquitination and proteosomal degradation.

c-Abl and Arg Phosphorylate Catalase:

To assess the potential role of c-Abl and Arg in regulating catalase, studies were performed to determine whether catalase is subject to tyrosine phosphorylation. Analysis of anti-Flag immunoprecipitates with anti-P-Tyr demonstrated tyrosine phosphorylation of catalase. Moreover, a similar analysis in the presence of MG132 showed that the ubiquitinated forms of catalase are phosphorylated on tyrosine.

To define potential phosphorylation sites, catalase was incubated with c-Abl and then subjected to tryptic digestion. Analysis of the fragments by HPLC separation and Edmon sequencing demonstrated phosphorylation of Y231 and Y386. Compared to wild-type catalase, mutation of Y231 to F resulted in a decrease in c-Abl-mediated tyrosine phosphorylation. A similar decrease in tyrosine phosphorylation was observed with the catalase (Y386F) mutant. The results also show that, in the presence of MG132, Arg-mediated tyrosine phosphorylation of ubiquitinated catalase is decreased for the Y231F and Y386F mutants. These findings indicate that catalase is phosphorylated on Y231 and Y386 by c-Abl and Arg and that these modifications are necessary for ubiquitination of catalase.

Ubiquitination and Stabilty of Catalase are Regulated by c-Abl/Arg Phosphorylation:

To determine whether catalase stability is directly regulated by c-Abl and Arg, expression of Flag-tagged catalase was compared to that of Flag-catalase (Y231F) and Flag-catalase(Y386F). Levels of the two Y→F mutants were higher than that found with wild-type catalase. Moreover, mutation of the PFNP motif to abrogate c-Abl and Arg binding resulted in increased catalase expression. In concert with these results, stability of catalase was increased by mutation of the Y231, Y386 or P293 sites. Ubiquitination of catalase(Y231F) and catalase(Y386F) was also substantially decreased compared to that of wild-type catalase. Similar results were obtained with the catalase(P293A) mutant.

To further define the effects of c-Abl, anti-Flag immunoprecipitates were analyzed from cells expressing Flag-catalase and Myc-tagged c-Abl. Ubiquitination of wild-type Flag-catalase was increased by c-Abl. By contrast, c-Abl had little effect on ubiquitination of the catalase mutants. Arg also increased ubiquitination of wild-type catalase, but not the Y→F or P→A mutants. These results demonstrate that tyrosine phosphorylation of catalase by c-Abl and Arg regulates catalase ubiquitination and stability.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that inhibits mitochondrial translocation of a protein kinase, the method comprising:
providing a cell;
subjecting the cell to a cellular stress, wherein the cellular stress induces mitochondrial translocation of the protein kinase;
contacting the cell with a test compound; and
determining whether mitochondrial translocation of the protein kinase is decreased when the cell is contacted with the test compound,
the decrease being an indication that the test compound inhibits mitochondrial translocation of the protein kinase.

2. The method of claim 1, wherein the protein kinase is c-Abl.

3. The method of claim 1, wherein the protein kinase is PKC delta.

4. The method of claim 1, wherein the cellular stress comprises oxidative stress.

5. The method of claim wherein the cell is subjected to oxidative stress by contacting the cell with hydrogen peroxide ($H_2O_2$).

6. The method of claim 1, wherein the cellular stress comprises endoplasmic reticulum (ER) stress.

7. The method of claim 6, wherein the cell is subjected to ER stress by administering a substance to the cell that increases intracellular calcium pools or blocks transport of proteins from the ER to Golgi.

8. The method of claim 1, wherein the cellular stress comprises cytoskeletal stress.

9. The method of claim 1, wherein the cellular stress comprises genotoxic stress.

10. A method of identifying a compound that increases mitochondrial translocation of a protein kinase, the method comprising:
    providing a cell;
    contacting the cell with a test compound; and
    determining whether mitochondrial translocation of the protein kinase is increased when the cell is contacted with the test compound,
    the increase being an indication that the test compound increases mitochondrial translocation of the protein kinase.

11. A method of identifying a protein that is translocated to the mitochondria upon the induction of oxidative stress, the method comprising:
    providing a cell;
    subjecting the cell to a oxidative stress; and
    identifying a protein that is translocated to the mitochondria of the cell.

12. The method of claim 11, wherein the cell is subjected to oxidative stress by contacting the cell with $H_2O_2$.

13. The method of claim 11, wherein detecting the mitochondrial translocation of the protein comprises isolating the mitochondria of the cell and determining the presence or amount of the protein in the mitochondria as compared to the presence or amount of the protein in the mitochondria of a cell not subjected to oxidative stress.

14. The method of claim 2, wherein the cellular stress comprises oxidative stress.

15. The method of claim 14, wherein the cell is subjected to oxidative stress by contacting the cell with $H_2O_2$.

16. The method of claim 3, wherein the cellular stress comprises oxidative stress.

17. The method of claim 16, wherein the cell is subjected to oxidative stress by contacting the cell with $H_2O_2$.

18. The method of claim 10, wherein the protein kinase is c-Abl.

19. The method of claim 10, wherein the protein kinase is PKC delta.

* * * * *

UNITED STATES PATENT AND TRADEMARK OFFICE
CERTIFICATE OF CORRECTION

PATENT NO. : 7,118,862 B2 Page 1 of 1
APPLICATION NO. : 10/125003
DATED : October 10, 2006
INVENTOR(S) : Donald W. Kufe, Rima Kaddurah-Daouk and Ralph R. Weichselbaum It is certified that error appears in the above-identified patent and that said Letters Patent is hereby corrected as shown below:

<u>Column 32,</u>
Line 57, after "claim" insert --4--.

<u>Column 33,</u>
Line 18, replace "the cell to a oxidative stress" with -- the cell to oxidative stress --.

Signed and Sealed this

Thirtieth Day of October, 2007

JON W. DUDAS
*Director of the United States Patent and Trademark Office*